United States Patent [19]

Sienkiewicz

[11] Patent Number: 4,775,634
[45] Date of Patent: Oct. 4, 1988

[54] METHOD AND APPARATUS FOR MEASURING DISSOLVED ORGANIC CARBON IN A WATER SAMPLE

[75] Inventor: Peter M. Sienkiewicz, Randolph, Mass.

[73] Assignee: Servomex Company, Norwood, Mass.

[21] Appl. No.: 893,832

[22] Filed: Aug. 6, 1986

[51] Int. Cl.[4] .......................................... G01N 33/18
[52] U.S. Cl. ..................................... 436/146; 422/80; 210/758
[58] Field of Search ........................ 436/146; 422/80; 210/758

[56] References Cited

U.S. PATENT DOCUMENTS

| | | | |
|---|---|---|---|
| 3,607,071 | 9/1971 | Staffin | 436/146 |
| 3,672,841 | 6/1972 | Freeman, Jr. et al. | 436/146 |
| 3,771,962 | 11/1973 | Winterhalter et al. | 436/146 |
| 3,840,341 | 10/1974 | Rogers | 436/146 |
| 3,854,881 | 12/1974 | Cohen | 436/146 X |
| 3,958,941 | 5/1976 | Regan | |
| 3,958,945 | 5/1976 | Takahashi | |
| 4,095,951 | 6/1978 | DiCola et al. | 436/146 |
| 4,217,108 | 8/1980 | Meltzer et al. | |
| 4,248,593 | 2/1981 | Blunck | |
| 4,277,438 | 7/1981 | Ejzak | 422/80 |
| 4,288,229 | 9/1981 | Mar | 436/146 |
| 4,293,522 | 10/1981 | Winkler | 422/80 |
| 4,344,918 | 8/1982 | Takahashi | 422/80 |
| 4,619,902 | 10/1986 | Bernard | 436/146 X |
| 4,626,413 | 12/1986 | Blades et al. | 422/68 X |

FOREIGN PATENT DOCUMENTS

| | | | |
|---|---|---|---|
| 2823587 | 12/1979 | Fed. Rep. of Germany | 436/146 |
| 395755 | 1/1974 | U.S.S.R. | 436/146 |

OTHER PUBLICATIONS

Soier, et al., "Photochemical Method of Determining Organic Carbon," Novocherkassk Hydrochemical Institute *Hydrochemical Materials*, 46, pp. 1-15.

*Primary Examiner*—Barry S. Richman
*Assistant Examiner*—Jill Johnston
*Attorney, Agent, or Firm*—Marjama & Pincelli

[57] ABSTRACT

The apparatus and method for measuring the amount of dissolved organic carbon in a sample utilizes an oxidation chamber wherein the dissolved organic carbon is ionized and a separate measuring chamber whereby an oxygen containing gas is pumped between the two chambers. The process water to be measured is used as both the reference water and sample.

7 Claims, 1 Drawing Sheet

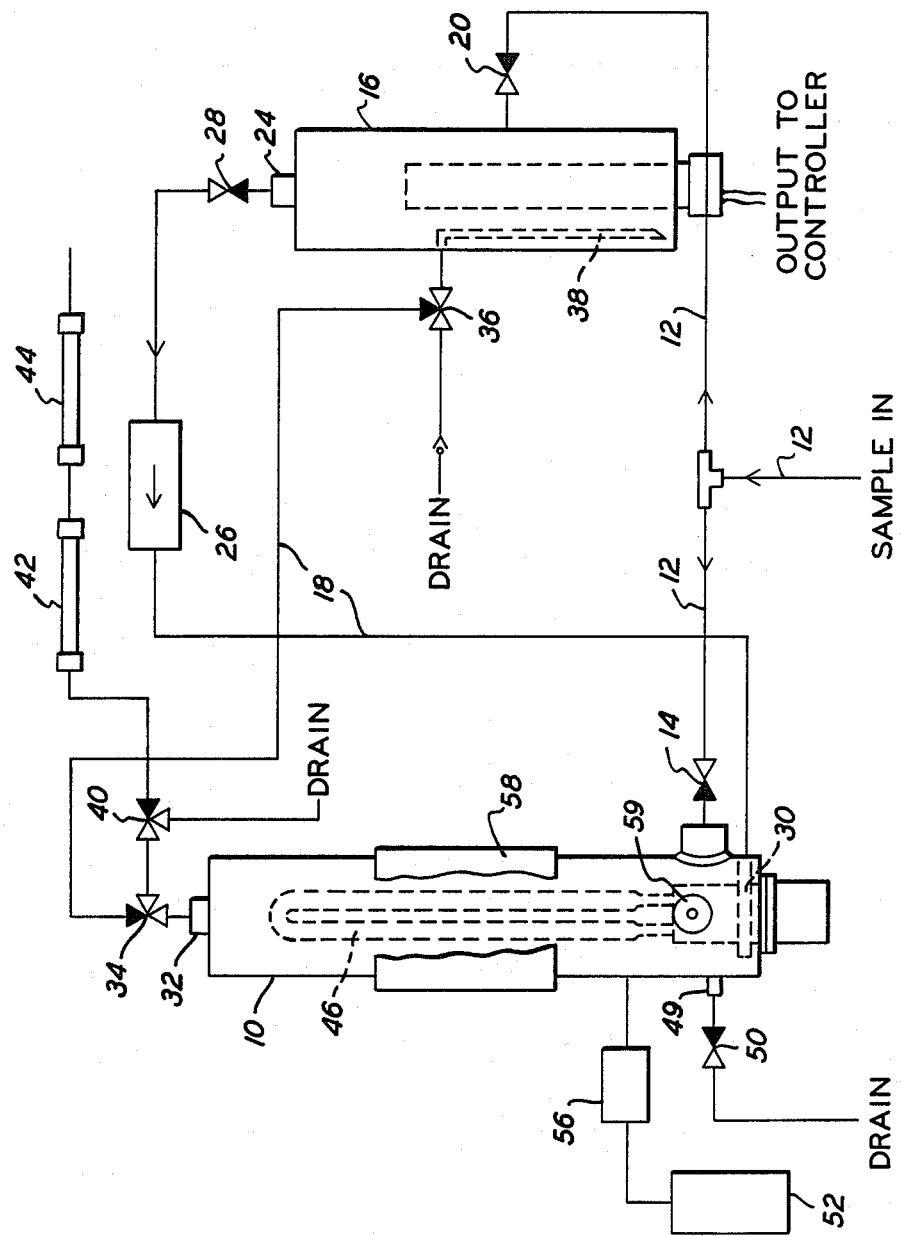

METHOD AND APPARATUS FOR MEASURING DISSOLVED ORGANIC CARBON IN A WATER SAMPLE

BACKGROUND OF THE INVENTION

The present invention is directed to a method and apparatus for measuring the organic carbon content of an aqueous solution.

It has become important that organic carbon measurement devices detect organic contents levels of less than ten parts per billion. The prior art has been limited to detection levels greater than twenty parts per billion TOC.

U.S. Pat. No. 3,958,941 discloses an organic carbon analyzer wherein a deionizing cartridge assembly is used to generate a high purity reference water upon which future measurements are based. Since the resin material in the cartridge assembly is organic in nature, the constant recirculation that occurs in such a device inparts a relatively high organic content to the overall system or background water. The detection limits of such a device is limited by the random changes that occur in the organic content of the system water. It has been found in practice that the background value will vary on an average of plus or minus ten parts per billion Total Organic Content (TOC) at one standard deviation. This indicates that the detection limits of the device is in the range of twenty parts per billion. This renders the device substantially incapable of analyzing the TOC of ultra high purity water process streams used, for example, in a semiconductor industry where TOC is typically below twenty parts per billion.

Other organic measuring devices exist which use a single chamber device, for example the organic analyzer produced by Anatel Model A-100. In this device, a single chamber is used for the oxidation conductivity measurement. Since only a single chamber is used biproducts produced during oxidation can cause a significant error in measurement.

Applicant has developed an improved method and apparatus whereby detection levels of substantially less than ten parts per billion can be measured. Additionally, applicant's invention provides other advantages not taught or suggested in the prior art.

SUMMARY OF THE PRESENT INVENTION

The apparatus and method of the present invention utilizes an oxidation chamber wherein the dissolved organic carbon is ionized and a separate measuring chamber whereby an oxygen containing gas is pumped between the two chambers. The process water to be measured is used as both the reference water and sample.

DESCRIPTION OF THE DRAWING

The drawing is an overall diagram in partial cross section of an apparatus for determining the amount of organic carbon in aqueous solution or in water according to the preferred embodiment of the present invention.

DETAILED DESCRIPTION OF THE INVENTION

Referring to the drawing, there is illustrated a diagram of the apparatus used to measure the organic content in an aqueous solution in the presence of an oxygen containing gas such as air. A closed oxidation chamber 10 is provided for receiving a water sample from a process feed line 12 through input valve 14. A closed measuring chamber 16 is provided and is connected to oxidation chamber 16 by gas loop 18. The measuring chamber 16 is also connected to the process feed line 12 through input valve 20. The top of closed measuring chamber 16 is provided with an output port 24 and is connected to a pump 26 through output valve 28. The output port of pump 26 is connected to the oxidation chamber 10 by means of an aspiration tube 30 located substantially at the bottom of the oxidation chamber 10. The oxidation chamber 10 has an outlet port 32 which is connected to the output valve 34. One port of valve 34 is connected to the measuring chamber 16 through valve 36. Valve 36 has one port connected to a measuring chamber aspiration tube 38 disposed substantially at the bottom of the measuring chamber. The valve 36 is also provided with a port which empties to drain. The valve 34 is also connected to a gas intake drain valve 40 which has one port connected to drain and a second port connected to atmosphere or other oxygen containing gas through filters 42, 44 which filter out $CO_2$ and organic vapors present in the gas. In the particular embodiment illustrated filters 42, 44 are connected to atmosphere. Disposed within the oxidation chamber 10 is an ultraviolet lamp 46 (shown in dash lines) for irradiating the sample water to convert the organic matter present into carbon dioxide which will be aspirated into measuring chamber 16 until an equilibrium of carbon dioxide is reached between the oxidation chamber 10 and measuring chamber 16.

The oxidation chamber is further provided with a outlet port 49 which is connected to drain through valve 50.

In the particular embodiment illustrated, a reservoir 52 of persulfate solution is connected to oxidation chamber 16 through input line 54 and check valve 55. An appropriate amount of persulfate solution is dispensed into oxidation chamber at the desired time by dispensing pump 56.

The ultraviolet lamp 46 is connected to a power source (not shown) which is activated at the appropriate time by a microprocessor in the control part of the apparatus (not shown). The control portion of the apparatus of the present invention does not form a part of the present invention and can be easily designed by one of ordinary skill in the art.

In the particular embodiment illustrated, a heater is wrapped around the oxidation chamber so as to control the temperature of the water sample within the oxidation chamber. The heater 58 is operated such that the temperature of the water is maintained at a temperature of at least 50° C.

The oxidation chamber is further provided with an injection port 59 to allow a standard solution of a known organic content to be inserted into the system for calibration of the device.

The measuring chamber 16 determines the amount of organic content of the sample in the same manner as clearly set forth in U.S. Pat. No. 3,958,941 previously discussed.

In order to fully understand the present invention, the operation of the device will now be discussed. The apparatus is first flushed out wherein valves 14, 20 are energized so as to allow sample water under pressure in line 12 to enter both the oxidation chamber 10 and measuring chamber 16. Valves 34 and 40 associated with oxidation chamber 10 and valve 36 associated with measuring chamber 16 are maintained in their normally open position to allow excess process water to flow to drain. This state is maintained as long as desired to remove all traces of any previous sample. Applicant has found that a flushing cycle of approximately two minutes is sufficient to flush the system. At the appropriate time valves 14 and 20 are closed thereby trapping a sample of water in the oxidation chamber and measuring chamber 10, 16 respectively. The water sample in the oxidation chamber is that sample upon which measurements will be taken, while the water in the measuring chamber 16 will become the reference water. At this point in time, the heater 58 is turned on and will continue to operate until the oxidation chamber is maintained at approximately 50° Centigrade. This temperature is maintained in order to assure complete oxidation of the organic materials present in the sample water. At this point in time valves 40 and 50 are opened for a sufficient amount of time to allow a metered amount of sample water to drain through valve 50 from the oxidation chamber creating a head space 60 in oxidation chamber 10. In the particular embodiment illustrated 100 milliliters of the sample water is allowed to drain. The air or other oxygen containing gas that enters the chamber during this process is passed through filters 42 and 44 for removing any carbon dioxide or organic vapors that may be present. This is done to remove any possibility of outside interferences with the meaurement. Also, as can be seen from the drawing a small head space 62 is present in the measuring chamber 16. This is obtained during the initial filling of measuring chamber 16 from feed line 12. During initial filling of measuring chamber 16 excess water is allowed to go to drain through valve 36 which is connected to chamber 16 through exit port 37. In the particular embodiment illustrated exit port is disposed below the top of chamber 16. Accordingly, not all of the air initially present will be exhausted as valve 28 is maintained in the closed state. Since the sample feed water is under pressure the head space 62 will be compressed. After the apparatus is run through several cycles, the size of the head space 62 will stabilize. After headspace 60 is provided, pump 26 is activated and a flowing gas stream is established between the oxidation chamber 10 and measuring chamber 16. In the particular embodiment illustrated pump 26 is an oscillating pump as this type of pump can handle small amounts of liquid that may be present in the flow of gas. Operation of the oscillating pump causes the air in the gas loop 18 to exit aspiration tube 30. Applicant has found that preferably the aspiration tube is somewhat circular in shape to conform to the shape of the chamber 16 and is placed at the bottom of the oxidation chamber 10. Applicant found most improved results occur when the oxidation chamber 16 is disposed in a substantially vertical position as this results in good mixing of the gas with the water in oxidation chamber 10. Likewise the aspiration tube 38 in measuring chamber 16 is placed substantially at the bottom of measuring chamber 16 so as to improve the mixing of the gas with the water.

The aspirating gas in both oxidation chamber and measuring chamber is maintained for a predetermined amount of time to allow for the equilibrium of inorganic source such as free carbon dioxide or bicarbonate. In the particular embodiment illustrated applicant has found two minutes is sufficient so as to allow conductivity changes due to inorganic sources to be measured and accounted for and an initial reference point is obtained.

Once the initial reference point is obtained with regard to the amount of inorganic content of the sample, the ultraviolet lamp 46 is activated. Applicant has found that converting of the organic matter in the water sample may be enhanced by introducing at this point in time a predetermined amount of persulfate oxidizing agent. Accordingly, the dispensing pump 50 is activated so as to introduce a predetermined amount of persulfate into the oxidation chamber. The organic matter present in the sample water in the oxidation chamber is oxidized to carbon dioxide. This carbon dioxide passes through gas loop 18 which causes further conductivity changes in the sample in the measuring chamber 16. The pump is maintained for a predetermined amount of time so as to allow the carbon dioxide to reach an equilibrium point between the oxidation chamber and measuring chamber. At this point in time the change in conductivity that has occured in the measuring chamber is measured and is proportional to the total organic carbon concentration of the water sample.

The foregoing process can be repeated for each additional sample to be measured.

The apparatus also provides means for calibration of the device by use of an injection port 59. Calibration may be performed after a water sample has been put through an analysis cycle and an initial reference measurement taken. Thereafter a known quantity of a standard solution is inserted into the oxidation chamber and an analysis cycle is allowed to continue until completion of the ionization of the standard and a second measurement is then taken. From the initial and second measurements, the device can be readily calibrated.

Applicant's process provides distinct advantages over the process disclosed in U.S. Pat. No. 3,958,941 to Reagan. The Reagan device uses high purity reference water upon which measurements are based. Applicant's invention utilizes the deionized sample water in the process stream as both the reference water and sample water. This is particularly advantageous as the use of a deionzing cartridge has limited capacity and must be replaced when exhausted. This, of course, provides additional cost and replacement required to carry out this process. Additionally, and even more importantly, the resin material in the cartridge assembly in Reagan is organic in nature. The constant recirculation that occurs in the Reagan device provides a relatively high organic content to the overall system or background water. Since the organic content of the sample is determined by first analyzing the background water, the detection limits of the Reagan device is limited by the random changes that occur in the organic content of the system water. Applicant has found in practice that the instrument value (the value obtained by carrying out an analysis without a sample to be measured) will vary on the average of plus or minus ten parts per billion TOC at one standard deviation. This indicates the detection limit of the device is in the range of twenty parts per billion TOC. This renders the device incapable of analyzing TOC contents of modern high purity water process streams used for example in the semi-conductor industry where TOC is typically twenty parts per billion or below. By eliminating use of the deionizing cartridge this factor is eliminated. The device of the present invention in practice has a blank value that varies on the average of plus or minus 0.4 parts per billion TOC at one standard deviation. This indicates that the detection limit of the device is in the range of one part per billion TOC. This makes it well suited for use in high purity process water.

Other prior art devices such as the Anatel A-100 suffers substantial disadvantage in that it is a single-chambered device. The oxidation and conductivity measurements are performed in the same chamber. This severely limits the device in two ways. First, interferences in the conductivity measurements can occur due to substances other than $CO_2$ that might be produced during the oxidation. For example, if the organic substances being analyzed is 1,1,1 trichloroethane a common organic used as a solvent, oxidation would produce the following products:

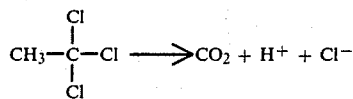

The hydrochloric acid that is produced as a biproduct of this oxidation is ionic in nature and contributes to the conductivity of the water in which it is dissolved. In fact, because hydrochloric acid is a strong acid and $CO_2$ is only weakly acidic, the conductivity contribution of the hydrochloric acid will be greater than that of the $CO_2$. The conductivity contribution of boths parts will be measured causing a significant error in the measurement.

The second limitation of the Anatel device is again due to the single chamber design. The use of persulfate oxidant is not possible. This is because the persulfate reagent itself is highly ionized. The conductivity contribution

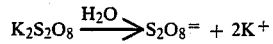

of the persulfate reagent would completely over shadow any contribution from $CO_2$ produced in the oxidation chamber.

The present invention overcomes the deficiencies of both the Reagan and Anatel devices.

What is claimed is:

1. An apparatus for measuring the amount of dissolved organic carbon present in a water sample wherein the sample water to be measured is also used as the reference water comprising:
    an oxidation chamber having an ultraviolet lamp disposed within the interior of said oxidation chamber for irradiating dissolved organic carbon present in the water sample thereby producing carbon dioxide;
    a measuring chamber;
    means for introducing the sample water into said oxidation chamber and said measuring chamber;
    a gas transmission loop connecting said oxidation chamber with said measuring chamber;
    means for detecting the initial inorganic carbon content as carbon dioxide of the sample water so as to provide an initial reference point;
    means for flowing at least a portion of the carbon dioxide produced in said oxidation chamber from said oxidation chamber through said gas transmission tube to said measuring chamber; and
    control means for determining the amount of carbon dioxide in said measuring chamber from said oxidation chamber, the including means for comparing the amount of carbon dioxide with the initial reference point amount of carbon dioxide being representative of the amount of dissolved organic carbon introduced into said apparatus.

2. The apparatus according to claim 1 further comprising filter means for filtering air which is introduced into said oxidation chamber.

3. The apparatus according to claim 1 further comprising means for introducing a predetermined amount of a solution of persulfate to the water sample in said oxidation chamber.

4. The apparatus according to claim 1 wherein said means for flowing at least a portion of said carbon dioxide from said oxidation chamber through said gas transmission tube to said measuring chamber comprises an oscillating pump.

5. The apparatus according to claim 1 wherein said oxidation chamber is provided with an injection port for introducing a test sample into said oxidation chamber.

6. A method for measuring an amount of dissolved organic carbon in a sample of water comprising the steps of:
    dividing a sample of water into said first and second samples,
    introducing said first sample of water to be measured into an oxidation chamber and said second sample into a measuring chamber;
    providing air in the oxidation chamber so as to create a head space;
    determining an initial amount of inorganic content of the second sample as carbon dioxide so as to establish an initial reference point;
    irradiating said first sample of water in the oxidation chamber with an ultraviolet light so as to produce carbon dioxide from dissolved carbon in said first sample of water;
    introducing a portion of said carbon dioxide present in the oxidation chamber into the measuring chamber; and
    measuring the amount of carbon dioxide present in said first sample in the measuring chamber and comparing the amount of carbon dioxide present with the initial reference point to adjust the inorganic carbon in said first sample whereby the amount is dissolved organic carbon is determined.

7. The method according to claim 6 further including introducing a persulfate into the oxidation chamber for enhancing the radiation of the dissolved carbon so as to more efficiently produce carbon dioxide.

* * * * *